(12) United States Patent
Hsieh

(10) Patent No.: US 10,850,128 B2
(45) Date of Patent: Dec. 1, 2020

(54) REAL-TIME, PARALLEL X-RAY TOMOSYNTHESIS

(71) Applicant: The Regents of the University of California, Oakland, CA (US)

(72) Inventor: Scott S. Hsieh, Anaheim, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/092,689

(22) PCT Filed: Apr. 10, 2017

(86) PCT No.: PCT/US2017/026802
§ 371 (c)(1),
(2) Date: Oct. 10, 2018

(87) PCT Pub. No.: WO2017/180513
PCT Pub. Date: Oct. 19, 2017

(65) Prior Publication Data
US 2019/0126070 A1 May 2, 2019

Related U.S. Application Data

(60) Provisional application No. 62/320,788, filed on Apr. 11, 2016.

(51) Int. Cl.
*A61N 5/10* (2006.01)
*A61B 6/02* (2006.01)
(Continued)

(52) U.S. Cl.
CPC .............. *A61N 5/1049* (2013.01); *A61B 6/00* (2013.01); *A61B 6/025* (2013.01); *A61B 6/06* (2013.01);
(Continued)

(58) Field of Classification Search
CPC ....... H04N 5/33; G06F 21/32; G06K 9/00597
See application file for complete search history.

(56) References Cited

U.S. PATENT DOCUMENTS 4,516,252 A 5/1985 Linde
7,933,010 B2 4/2011 Rahn
(Continued)

FOREIGN PATENT DOCUMENTS

WO 2017026802 2/2017

OTHER PUBLICATIONS

Benedict SH, et al. Stereotactic body radiation therapy: The report of AAPM task group 101. Med Phys. 2010; 37(8): 4078-4101.
(Continued)

*Primary Examiner* — Hugh Maupin
(74) *Attorney, Agent, or Firm* — Quarles & Brady LLP

(57) ABSTRACT

A device for performing tomosynthesis in real time is described. Multiple imaging sources (such as x-ray sources) may be energized in parallel and collimated towards a field of view. Objects within the field of view cast shadows onto one or more detectors. An imaging system may read the one or more detectors and acquire multiple views corresponding to the multiple imaging sources to produce a reconstructed image of an object of interest. From this reconstructed image, a target of the radiation therapy can be located, and the delivery of the radiation can be adjusted, as needed. The approach provides a real-time tomosynthesis design that can produce enhanced contrast for guidance of, for example, lung tumor treatment. Higher frame rates can be achieved to better compensate for changes in the position of the target during radiation therapy due to, for example, respiratory or cardiac motion.

30 Claims, 12 Drawing Sheets

(51) Int. Cl.
| | |
|---|---|
| A61B 8/13 | (2006.01) |
| A61B 6/00 | (2006.01) |
| A61B 6/06 | (2006.01) |
| G01T 1/161 | (2006.01) |
| G01T 1/17 | (2006.01) |
| G01T 7/00 | (2006.01) |
| G06T 11/00 | (2006.01) |
| A61B 6/04 | (2006.01) |
| A61B 6/12 | (2006.01) |

(52) U.S. Cl.
CPC .......... *A61B 6/4007* (2013.01); *A61B 6/461* (2013.01); *A61B 6/54* (2013.01); *A61B 8/13* (2013.01); *A61N 5/1037* (2013.01); *A61N 5/1045* (2013.01); *A61N 5/1067* (2013.01); *G01T 1/161* (2013.01); *G01T 1/17* (2013.01); *G01T 7/00* (2013.01); *G06T 11/006* (2013.01); *A61B 6/0407* (2013.01); *A61B 6/0457* (2013.01); *A61B 6/12* (2013.01); *A61B 6/4014* (2013.01); *A61B 6/4085* (2013.01); *A61N 5/1068* (2013.01); *A61N 2005/1061* (2013.01); *G06T 2211/424* (2013.01)

(56) References Cited

U.S. PATENT DOCUMENTS

| | | | |
|---|---|---|---|
| 8,934,605 | B2 | 1/2015 | Maurer |
| 2009/0086889 | A1 | 4/2009 | Hashemi |
| 2010/0189223 | A1* | 7/2010 | Eaton .................... G21K 1/025 378/68 |
| 2012/0008735 | A1 | 1/2012 | Maurer |
| 2012/0033790 | A1 | 2/2012 | Wilfley |
| 2012/0163531 | A1 | 6/2012 | Zhang |
| 2012/0257710 | A1 | 10/2012 | Funk |
| 2015/0043712 | A1 | 2/2015 | Wang |
| 2015/0238159 | A1 | 8/2015 | Al Assad |
| 2015/0265223 | A1 | 9/2015 | Simon |
| 2016/0000393 | A1* | 1/2016 | Vedantham ............ A61B 6/025 378/27 |
| 2016/0256128 | A1* | 9/2016 | Wang ...................... A61B 6/54 |

OTHER PUBLICATIONS

Berbeco RI, et al. Residual motion of lung tumours in gated radiotherapy with external respiratory surrogates. Phys Med Biol. 2005; 50(16): 3655.

Chang JY, et al. Stereotactic ablative radiotherapy versus lobectomy for operable stage I non-small-cell lung cancer: A pooled analysis of two randomised trials. The Lancet Oncology. 2015; 16(6): 630-637.

Clark K, et al. The cancer imaging archive (TCIA): Maintaining and operating a public information repository. J Digital Imaging. 2013; 26(6): 1045-1057.

Corradetti MN, et al. Central-airway necrosis after stereotactic body-radiation therapy. N Engl J Med. 2012; 366(24): 2327-2329.

Hsieh, S.S. et al., Real-time tomosynthesis for radiation therapy guidance, American Association of Physicists in Medicine, International Journal of Medical Physics Research and Practice, Aug. 24, 2017, vol. 44, p. 5584-5594, John Wiley & Sons, Inc., United States.

Hsieh, S.S., Feasibility of real-time tomosynthesis for lung tumor tracking, Radiation Journal of Oncology, Poster Presentation, Oct. 1, 2016, United States.

International Search Report and Written Opinion for PCT/US2017/026802, dated Jun. 16, 2017, 10 pages.

Keall PJ, et al. The management of respiratory motion in radiation oncology report of AAPM task group 76a). Med Phys. 2006; 33(10): 3874-3900.

Loo BW,Jr, et al. Stereotactic ablative radiotherapy for the treatment of refractory cardiac ventricular arrhythmia. Circ Arrhythm Electrophysiol. Jun. 2015; 8(3): 748-750.

Ma L, et al. Nonrandom intrafraction target motions and general strategy for correction of spine stereotactic body radiotherapy. International Journal of Radiation Oncology* Biology* Physics. 2009; 75(4): 1261-1265.

Maltz JS, et al. Fixed gantry tomosynthesis system for radiation therapy image guidance based on a multiple source x-ray tube with carbon nanotube cathodes. Med Phys. 2009; 36(5): 1624-1636.

Mazin SR, et al. Inverse-geometry volumetric CT system with multiple detector arrays for wide field-of-view imaging. Med Phys. 2007; 34: 2133.

Milano MT, et al. A prospective pilot study of curative-intent stereotactic body radiation therapy in patients with 5 or fewer oligometastatic lesions. Cancer. 2008; 112(3): 650-658.

Murphy MJ, et al. The management of imaging dose during image-guided radiotherapy: Report of the AAPM task group 75. Med Phys. 2007; 34(10): 4041-4063.

Negoro Y, et al. The effectiveness of an immobilization device in conformal radiotherapy for lung tumor: Reduction of respiratory tumor movement and evaluation of the daily setup accuracy. International Journal of Radiation Oncology* Biology* Physics. 2001; 50(4): 889-898.

Pan H, et al. Clinical practice patterns of lung stereotactic body radiation therapy in the United States: A secondary analysis. Am J Clin Oncol. Jun. 2013; 36(3): 269-272. PMCID: PMC3396796.

Sartain L, et al. SU-EJ-56: Static gantry digital tomosynthesis from the beam's-eye-view. Med Phys. 2015; 42(6): 3276-3276.

Rieber J, et al. Stereotactic body radiotherapy (SBRT) for medically inoperable lung metastases—a pooled analysis of the german working group "stereotactic radiotherapy". Lung Cancer. 2016; 97: 51-58.

Seppenwoolde Y, et al. Precise and real-time measurement of 3D tumor motion in lung due to breathing and heartbeat, measured during radiotherapy. International Journal of Radiation Oncology* Biology* Physics. 2002; 53(4): 822-834.

Shirvani SM, et al. Lobectomy, sublobar resection, and stereotactic ablative radiotherapy for early-stage non-small cell lung cancers in the elderly. JAMA surgery. 2014; 149(12): 1244-1253.

Solomon EG, et al. In: Scanning-beam digital x-ray (SBDX) system for cardiac angiography. Proc. SPIE; 1999. p. 246-257.

Speidel MA, et al. Scanning-beam digital x-ray (SBDX) technology for interventional and diagnostic cardiac angiography. Med Phys. 2006; 33: 2714.

Timmerman R, et al. Excessive toxicity when treating central tumors in a phase II study of stereotactic body radiation therapy for medically inoperable early-stage lung cancer. J Clin Oncol. Oct. 20, 2006; 24(30): 4833-4839.

Vandemeulebroucke J, et al. In: The POPI-model, a point-validated pixel-based breathing thorax model. XVth International conference on the use of computers in radiation therapy (ICCR); 2007. p. 195-199.

Widder J, et al. Pulmonary oligometastases: Metastasectomy or stereotactic ablative radiotherapy; Radiotherapy and Oncology. 2013; 107(3): 409-413.

Yousefi S, et al. Complications of thoracic computed tomography-guided fiducial placement for the purpose of stereotactic body radiation therapy. Clinical lung cancer 2007; 8(4): 252-256.

European Patent Office, Extended European Search Report and European Search Opinion for application 17782917.3, dated Nov. 6, 2019.

* cited by examiner

REAL-TIME, PARALLEL X-RAY TOMOSYNTHESIS

CROSS-REFERENCE TO RELATED APPLICATIONS

This application represents the national stage entry of PCT/US2017/026802, filed Apr. 10, 2017, which claims benefit of U.S. Provisional Patent Application 62/320,788, filed Apr. 11, 2016. The contents of this application are hereby incorporated by reference as set forth in their entirety herein.

FIELD OF THE INVENTION

This invention relates generally to radiological imaging with enhanced frame rates, and in particular, to tomosynthesis well-suited for compensating for movements of patients during, for example, radiation therapy.

BACKGROUND

Patient motion has been a recurring problem in medical imaging. While computerized tomography (CT) and magnetic resonance imaging (MRI) offer unparalleled accuracy and resolution, data acquisition can require hundreds of milliseconds and may not adequately resolve changes in positions of targeted features resulting from, for example, respiratory or cardiac motion. With radiation therapy for lung cancer, for example, lung tumor motion is not adequately compensated for using only external surrogates such as respiratory gating, and the speed and path of motion may change between subsequent treatment fractions. In current lung stereotactic ablative radiation therapy (SABR) treatments, an additional internal target volume (ITV) margin is sometimes added to account for the uncertainty in the current position of a target. However, this increases the volume of tissue that receives radiation, and as a result, surrounding tissue that is "normal" (i.e., undiseased or otherwise untargeted) is more likely to receive lethal radiation. SABR treatments of central tumors in particular are associated with high levels of toxicity and tissue necrosis, even with gentler fractionation schedules.

Fluoroscopy has been a tool of choice for monitoring treatments or interventions because of its fast imaging times. However, the contrast obtained in fluoroscopy is insufficient for certain clinical applications. Tomosynthesis is sometimes used in an effort to improve conspicuity (or contrast) relative to fluoroscopy. In tomosynthesis, multiple x-ray images taken at different angles are reconstructed to show a region of interest. However, existing implementations of tomosynthesis require the serial acquisition of several views. For a typical flat panel imager acquiring data at 30 frames per second (fps), acquisition of a tomosynthetic image could require half a second or more, which does not provide the speed necessary for real-time feedback on changes in position.

It would therefore be useful to have a tomosynthesis system that can provide more rapid feedback to allow for real-time tracking of targets, allowing for adjustments to radiation delivery that are better able to compensate for patient motion during treatment.

SUMMARY OF THE PRESENT DISCLOSURE

In exemplary implementations, the disclosed systems and methods use multiple imaging sources to image a (potentially moving) target with enhanced speed and contrast. The imaging sources may simultaneously illuminate a field of view (that includes a target of interest), and one or more detectors can be used to receive the beams. In certain configurations, if the field of view is sufficiently small, a single detector (e.g., a flat panel detector) could be used by, for example, assigning different sectors on the detector to different sources. The images can then be combined to form a reconstructed image of the target. Such a real-time tomosynthesis system can provide guidance for radiation therapy for applications in which fluoroscopy or ultrasound provide insufficient contrast, and/or diagnostic scanners such as MRI or CT are too slow or unavailable in the clinical workflow. This tomosynthesis approach could resolve, for example, cardiac or respiratory motion during radiation treatments, such as treatments for lung cancer.

An exemplary device for parallel tomosynthesis, in certain configurations, includes of a plurality of small x-ray sources that are tightly collimated down to a small region of interest in a patient. These x-ray sources may be energized substantially simultaneously or in rapid succession (e.g., as rapid as the controller may instruct the imaging sources and the imaging sources may be energized in sequentially). After traveling through the patient, the images can be detected simultaneously in a single readout of an x-ray detector, and used to produce a reconstructed image. The reconstructed image can be used to make adjustments to the delivery of high-energy treatment radiation to a moving target.

An exemplary method for image guidance during high-energy radiation therapy, in certain implementations, may use a plurality of x-ray sources that are energized substantially simultaneously or in rapid succession to image a region of interest within a patient. A single detector may be used to receive radiation simultaneously passing through the patient. The information received at the detector can be reconstructed to form an image. Based on this information, for example, the location of a target may be identified, and the delivery of the high-energy radiation may be adjusted as needed.

Additional advantages and features of the invention will be apparent from the remainder of this document in conjunction with the associated drawings.

DETAILED DESCRIPTION OF THE PRESENT DISCLOSURE

Figure 1A:
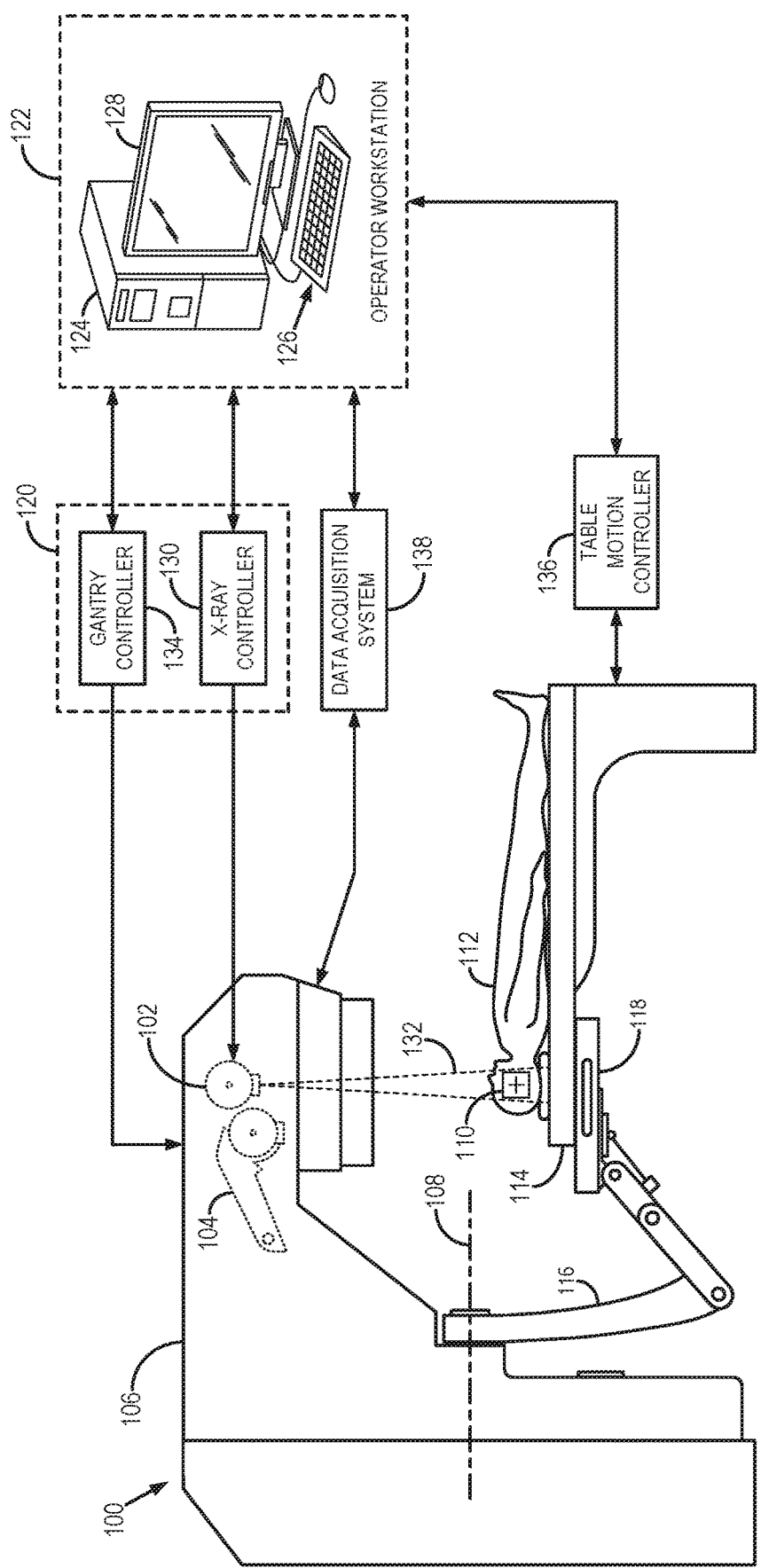
FIG. 1A depicts an example radiation therapy system with which exemplary real-time tomosynthesis devices can be implemented.
Figure 1B:
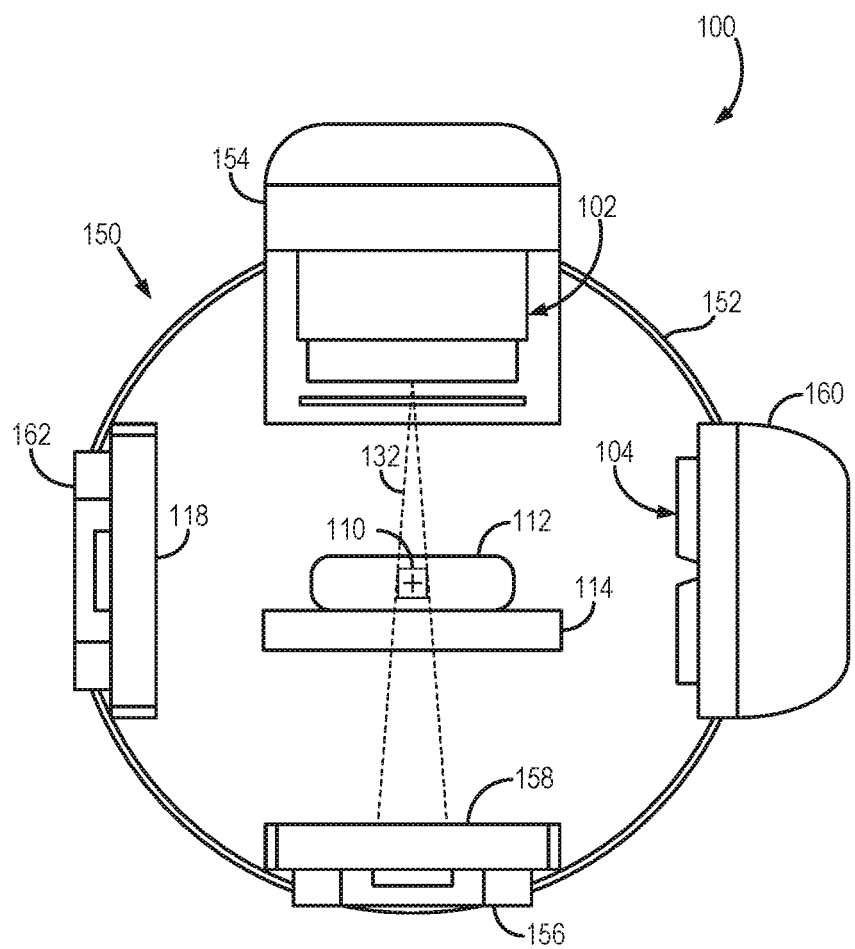
FIG. 1B depicts another radiation therapy system with which exemplary real-time tomosynthesis devices can be implemented.

FIGS. 1A and 1B depict radiation therapy systems which may be used in conjunction with exemplary implementations of the present invention. Referring to FIG. 1A, an example of an image-guided radiation therapy ("IGRT") system 100 includes a therapeutic (treatment) x-ray source 102 and a diagnostic (imaging) x-ray source 104, both of which are housed at an end of a first rotatable gantry 106 that rotates about a pivot axis 108. The first rotatable gantry 106 allows the therapeutic x-ray source 102 and the diagnostic x-ray source 104 to be aligned in a desired manner with respect to a target volume 110 in a subject 112 positioned on a patient table 114. A second rotatable gantry 116 is rotatably attached to the first rotatable gantry 106 such that the second rotatable gantry 116 is able to rotate about the pivot axis 108.

Positioned at one end of the second rotatable gantry 116 is an electronic portal imaging device (EPID), such as x-ray imager/detector 118. The x-ray detector 118 functions as a diagnostic image device when receiving x-rays from the diagnostic x-ray source 104, and can also function as a portal image device when receiving x-rays from the therapeutic x-ray source 102. The x-ray detector 118 may contain a number of detector elements (e.g., an array of detector elements) that together sense the projected x-rays that pass through the subject 112. Each detector element produces an electrical signal that represents the intensity of an x-ray beam impinging on that detector element and, hence, the attenuation of the beam as it passes through the subject 112.

The second rotatable gantry 116 can also include an articulating end that can pivot about one or more points. The pivoting motion provided by such points allows the x-ray detector 118 to be moved within one or more dimensions, such as within a two-dimensional plane. In other configurations, the x-ray detector 118 can be maintained in a fixed position on the second rotatable gantry 116.

A control mechanism 120 controls the rotation of the first rotatable gantry 106 and the second rotatable gantry 116, as well as operation of the therapeutic x-ray source 102 and the diagnostic x-ray source 104. The IGRT system 100 includes an operator workstation 122, which may include a processor 124 that receives commands and scanning parameters from an operator via an input 126 or from a memory or other suitable storage medium. The input may be a keyboard, a mouse, a touch screen, or other suitable input mechanism. An associated display 128 allows the operator to observe data from the computer 122, including images of the subject 112 that may be used to review or modify the treatment plan, and to position the subject 112 by way of appropriately adjusting the position of the patient table 114. The operator supplied commands and parameters may also be used by the computer 120 to provide control signals and information to the control mechanism 120.

The therapeutic x-ray source 102 is controlled by an x-ray controller 130 that forms a part of the control mechanism 120 and which provides power and timing signals to the therapeutic x-ray source 102. The x-ray controller 130 also provides power and timing signals to the diagnostic x-ray source 104. In some configurations, the x-ray controller 130 can include two independent controllers for controlling the therapeutic x-ray source 102 and the diagnostic x-ray source 104, and in other configurations a single controller can control both x-ray sources.

The therapeutic x-ray source 102 produces a radiation beam 132, or "field," in response to control signals received from the x-ray controller 130. The diagnostic x-ray source 104 projects a cone-beam of x-rays toward the x-ray detector 118. A gantry controller 134, which forms a part of the control mechanism 120, provides control signals to the first rotatable gantry 106 to control the rotational speed and position of the first rotatable gantry 106. In response to such control signals, the first rotatable gantry 106 is moved to change position and the gantry angle, $\Theta_i$, of the therapeutic x-ray source 102 and the diagnostic x-ray source 104. The gantry controller 134 connects with the operator workstation 122 so that the first rotatable gantry 106 may be rotated under computer control, and also to provide the operator workstation 122 with signals indicating the gantry angle, $\Theta_i$, to assist in that control. The gantry controller 134 also provides control signals to the second rotatable gantry 116 to change the position and the gantry angle, $\Theta_j$, of the x-ray detector 118.

The position of the patient table 114 may also be adjusted to change the position of the target volume 110 with respect to the therapeutic x-ray source 102, the diagnostic x-ray source 104, and the x-ray detector 118 by way of a table motion controller 136, which is in communication with the operator workstation 122.

A data acquisition system ("DAS") 138 samples data from the x-ray detector 118. In some configurations, the data sampled from the x-ray detector 118 is analog data and the DAS 138 converts the data to digital signals for subsequent processing. In other configurations, the data sampled from the x-ray detector 118 is digital data. The operator workstation 122, or a separate image reconstructor, receives x-ray data from the DAS 138 and performs image reconstruction. The reconstructed images can be stored in a mass storage device, or can be displayed on the display 128 of the operator workstation 122.

In an alternative configuration, shown in FIG. 1B, the IGRT system 100 includes a single rotatable gantry 150 that is movable to different positions for purposes of administering radiotherapy and for x-ray image acquisition of a subject 112, as described above.

The gantry 150 includes a ring 152, a first arm 154 extending from the ring 152 and to which the therapeutic x-ray source 102 is coupled, a second arm 156 extending from the ring 152 and to which a portal imager 158 is coupled, a third arm 160 extending from the ring 152 and to which the diagnostic x-ray source 104 is coupled, and a fourth arm 162 extending from the ring 152 and to which the x-ray detector 118 is coupled. The ring 152 is rotatable about an axis, such as the pivot axis 108 shown in FIG. 1A, to move the arms 154, 156, 160, 162 (and therefore the therapeutic x-ray source 102, portal imager 158, diagnostic x-ray source 104, and x-ray detector 118) about the axis.

The ring 152 can be driven in any conventional manner, including without limitation by a sun gear about which one or more planet gears can be driven, by a ring gear driven by one or more pinions or worm gears, or by a prime mover directly or indirectly coupled to an axle upon which a frame is mounted. The motion of the ring 152 can be controlled by the gantry controller 134.

The therapeutic x-ray source 102 can include a linear accelerator (i.e., a "linac") that produces a high-intensity x-ray beam that exits the therapeutic x-ray source 102 toward the target volume 110 in the subject 112. In other embodiments, the therapeutic x-ray source 102 can be replaced with other radiation therapy devices, such as any device capable of emitting electrons, gamma rays, and other types of radiation toward the target volume 110 in the subject 112. A variety of radiation-emitting devices capable of emitting a number of different types of radiation and adapted for radiotherapy exist and can be implemented in lieu of the therapeutic x-ray source 102.

By rotating the ring 152 the arm 154 also rotates, thereby rotating the therapeutic x-ray source 102 through a range of different positions about the target volume 110. This adjustment enables a user to change the trajectory of the radiation beam exiting from the therapeutic x-ray source 102, thereby enabling the user to direct the beam to different desired locations in or on the subject 112. The ring 152 can be rotatable through any range permitting this beam control. For example, the ring 152 can rotate through a range of 360 or more degrees in order to move the therapeutic x-ray source 102 through the same range, although smaller ranges of movement are also possible.

As noted above, a portal imager 158 is also coupled to the ring 152 via the second arm 156. The portal imager 158 can receive at least some of the radiation from the therapeutic x-ray source 102 in order to generate images of the subject 112. Any conventional portal imager 158 can be used for this purpose, such as radiographic film, flat-panel and other types of electronic portal imagers, and other conventional x-ray imaging devices.

The portal imager 158 is located opposite the therapeutic x-ray source 102 across the target volume 110, and can be oriented to receive radiation emitted from the therapeutic x-ray source 102 as described above. To this end, the portal imager 158 is located on the second arm 156 extending from the ring 152 at a location opposite the first arm 154.

By rotating the ring 152, the arm 156 supporting the portal imager 158 can also rotate, thereby rotating the portal imager 158 with the therapeutic x-ray source 102 through a range of different positions about the target volume 110. In this manner, the portal imager 158 can acquire patient images in the different positions of the therapeutic x-ray source 102. Although a portal imager 158 is illustrated in the IGRT system 110 shown in FIG. 2, in alternative configurations the IGRT system 110 has no portal imager 158.

As described above, the IGRT system 100 shown in FIG. 1B also includes a diagnostic x-ray source 104 and an x-ray detector 118 coupled to the gantry 150. The diagnostic x-ray source 104 is coupled to an arm 160 extending from the ring 152, and the x-ray detector 118 is coupled to an arm 162 extending from the ring 152.

By rotating the ring 152, the arms 160, 162 also rotate, thereby rotating the diagnostic x-ray source 105 and the x-ray detector 118 through respective ranges of positions about the target volume 110. This adjustment enables a user to move the diagnostic x-ray source 104 and x-ray detector 118 in order to acquire images of the subject 112 taken at different perspectives. The ring 152 can be rotatable through any range permitting such control. For example, the ring 152 can rotate through a range of 360 or more degrees in order to move the diagnostic x-ray source 104 and x-ray detector 118 through the same range, although smaller ranges of motion are also possible.

The diagnostic x-ray source 104 and x-ray detector 118 are located across the target volume 110 in circumferential positions spaced between the therapeutic x-ray source 102 and the portal imager 158. The diagnostic x-ray source 104 and x-ray detector 118 can be equally or unequally circumferentially spaced between the therapeutic x-ray source 102 and the portal imager 158. In the latter configuration, the diagnostic x-ray source 104 and x-ray detector 118 are located adjacent the therapeutic x-ray source 102 and the portal imager 158, respectively, which can provide increased access to the subject 112 at one or more circumferential positions. The exemplary tomosynthesis systems and methods disclosed herein can be implemented by, for example, integrating multiple imaging sources with system 100, as further discussed below. This allows for the repurposing of detector 118 (as well as the high-voltage power supply for the diagnostic x-ray source 104), as further discussed below.

Figure 2B:
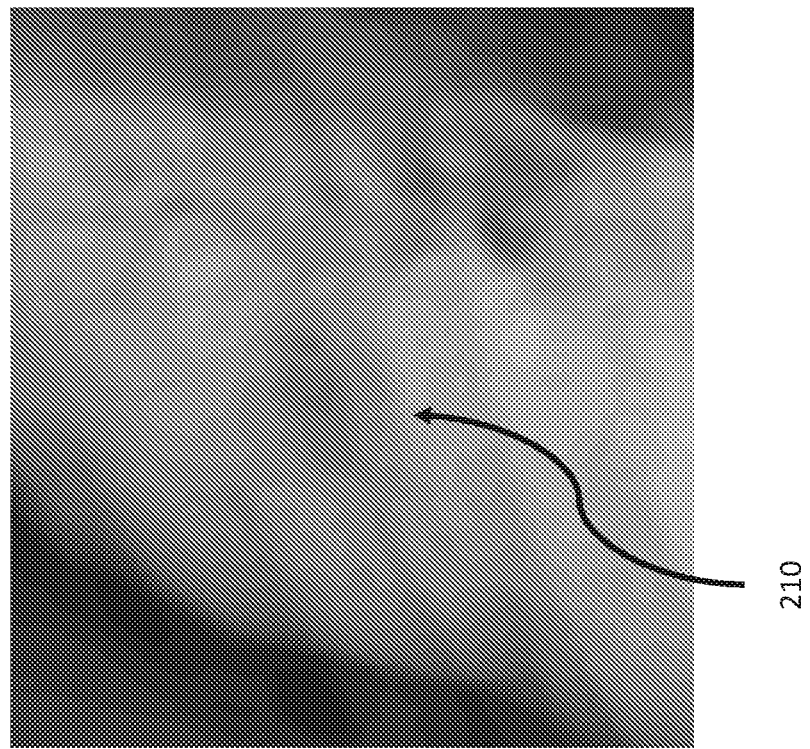
FIG. 2B is a sample detector image resulting from the radiation beam from the x-ray source of FIG. 2A.
Figure 2A:
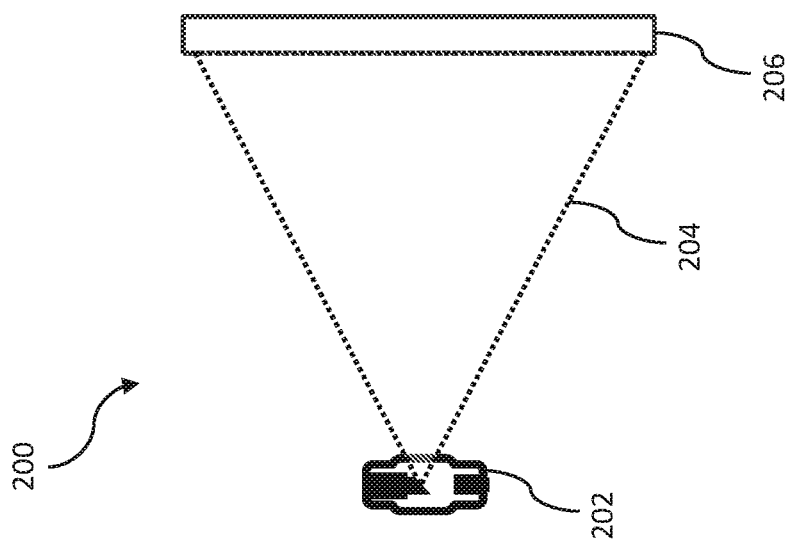
FIG. 2A depicts the geometry corresponding to the use of an x-ray source for fluoroscopy.
Figure 3B:
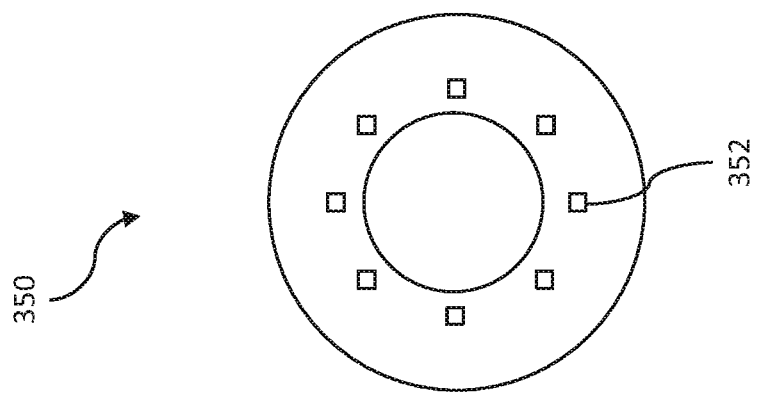
FIG. 3B depicts an exemplary collimator, viewed from isocenter, that may be used with the arrangement of FIG. 3A.
Figure 3A:
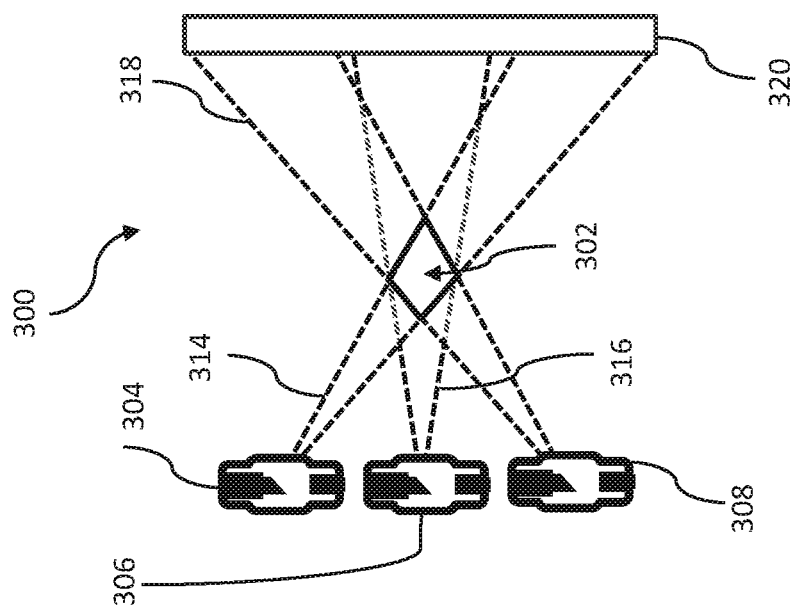
FIG. 3A shows an exemplary configuration for a tomosynthesis system that uses multiple imaging sources to intersect at and illuminate a field of view.

Referring to FIGS. 2A and 3A, the general geometric principle of exemplary real-time tomosynthesis systems is illustrated. FIG. 2A depicts conventional fluoroscopy performed with a source 202, which emits a wide x-ray beam 204 directed towards detector 206. With the exemplary tomosynthesis system 300 depicted in FIG. 3A, real-time tomosynthesis can be performed by simultaneous illumination of a field of view (FOV) 302 from multiple imaging sources 304, 306, 308, which emit imaging beams 314, 316, 318, respectively. A collimator 350 (shown in FIG. 3B) restricts the radiation beams 314, 316, 318 from each imaging source so as to intersect at the FOV 222. The exemplary collimator 350 includes multiple exit windows 352 for radiation beams. The radiation emanating from the imaging sources 304, 306, 308 may be collimated to, for example, 5 cm by 5 cm at isocenter, and then these rays diverge and arrive at the detector 320. These projections from the imaging beams 314, 316, 318 arrive on different sections of the detector 320. FIG. 2B shows the detector image for the fluoroscopy arrangement depicted in FIG. 2A, with a tumor 210 near the center of the image. Fluoroscopy provides poor tumor contrast with a large field of view (e.g., a 40 cm field of view). Compared to the fluoroscopy arrangement of FIG. 2A, image contrast is enhanced with tomosynthesis system 300 (see FIG. 5C, discussed below). While the FOV 222 with real-time tomosynthesis may be smaller, the frame rate of fluoroscopy is maintained. It is noted that the field of view may be enlarged if desired by using multiple detectors.

Figure 4:
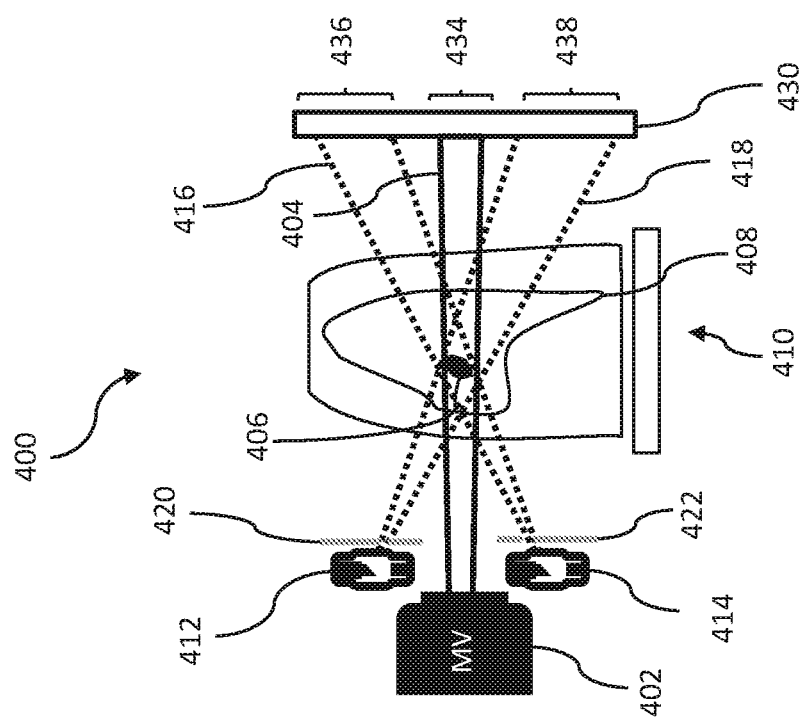
FIG. 4 depicts an exemplary tomosynthesis system that uses an imager/detector to receive imaging and treatment radiation beams in different regions/sectors.

Referring to FIG. 4, an exemplary tomosynthesis system 400 may include a treatment source 402, such as a megavolt (MV) x-ray source, for treating targeted cells (such as tumor cells). The treatment source 402 (which may be x-ray source 102 in the systems depicted in FIGS. 1A and 1B) emits a treatment beam 404 (solid line) at a tumor 406 in the lung 408 of patient 410. As shown, the chest of patient 410 is to the left, and the spine of the patient 410 is to the right. That is, from the perspective illustrated, the treatment beam 404 is directed in a sagittal plane with respect to patient 410.

System 400 also includes multiple imaging sources 412, 414, which may be kilovolt (kV) x-ray sources. Such imaging sources may be, for example, incorporated into the systems of FIGS. 1A and 1B by arranging the imaging sources about the therapeutic source 102 (for example, four sources in a ring separated from each other by 90 degrees). Imaging sources 412, 414 may emit imaging beams 416, 418 (dotted lines), respectively, directed such that they overlap/intersect at a region of interest/field of view that includes the tumor 406 being targeted by the treatment source 402. The system further includes collimators 420, 422 for collimating imaging beams 416, 418, respectively.

In FIG. 4, the beams emitted by the various sources are received at a single detector 430 (such as detector 118 in the systems depicted in FIGS. 1A and 1B), although in alternative implementations, multiple detectors may be used. In the configuration shown, the detector 430 may be divided ("sectored") into regions/sectors that are dedicated to beams from specified sources, such that no two beams would overlap in the areas of the detector that would receive the beams. Non-overlapping regions (of, for example, a flat-panel detector) may have circular, rectangular, or any other shape desired. Partially overlapping regions could also be used to expand the field of view, at the cost of reconstruction complexity and possible artifacts. Treatment beam 404 could thus be received in sector 434, and imaging beams 416, 418 could be received in sectors 436, 438, respectively. Sector 434 may be located, for example, at a central area of detector 430, and sectors 436 and 438 may have areas arranged around the central area, such as near the periphery of detector 430 (see FIG. 5B, discussed below).

It is noted that any number of imaging sources deemed suitable may be used, but preferably three or more sources are used in various implementations. In the exemplary configuration depicted in FIG. 5A, an exemplary treatment head 500 includes an array of eight imaging sources (x-ray tubes) 502 arranged in a ring (around a treatment source, not pictured). The treatment head 500 also includes a multileaf collimator 504. The x-ray tubes 502 surround the source of high-energy treatment radiation and are energized simultaneously or in quick succession, within the time of a single detector readout. The multileaf collimator 504 controls the distribution of the high-energy treatment radiation. The number of sources may vary, and can be based on, for example: cost considerations (i.e., the cost of additional imaging sources and installation/assembly thereof); space considerations (i.e., the number of imaging sources that would fit in the radiation therapy system); field of view considerations (i.e., additional projections could crowd the detector and necessitate a reduction in field of view); the safety of emitting additional x-rays beams at a patient, as balanced against the benefit of better imaging and thus enhanced compensation for patient motion via more accurate aiming of the treatment source (such that damage to targeted tissue is enhanced and/or collateral damage to healthy tissue is decreased); etc.

Figure 5B:
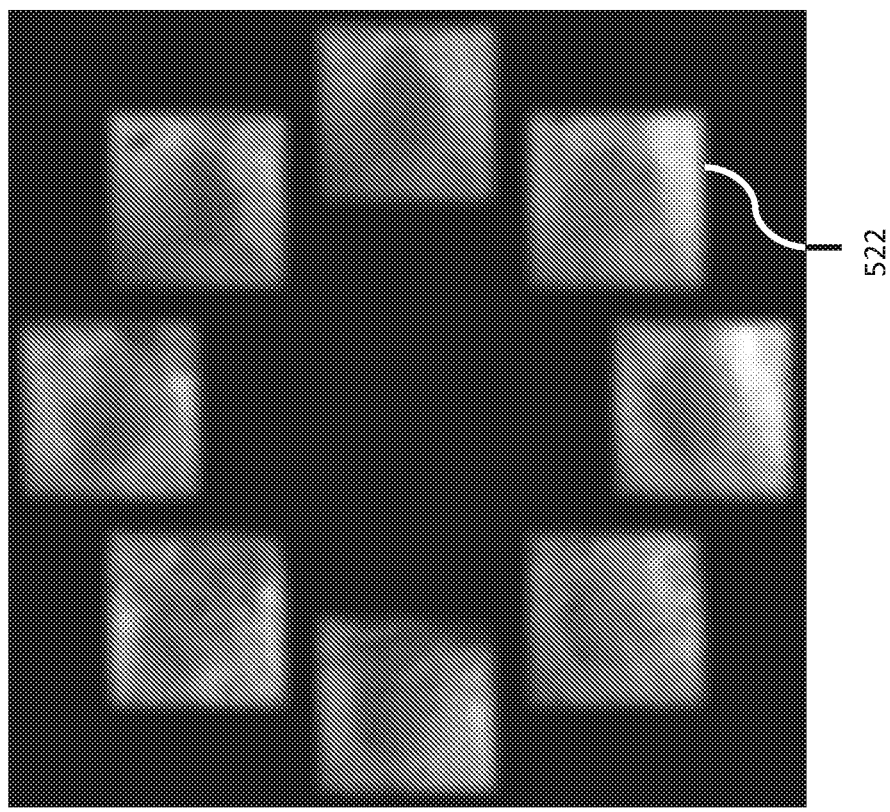
FIG. 5B shows an example of eight non-overlapping images (projections) formed using the imaging sources of FIG. 5A.
Figure 5A:
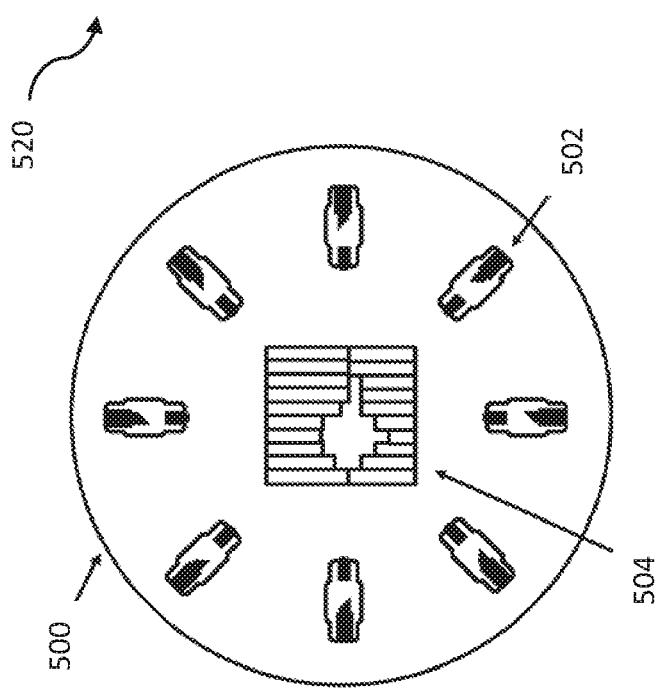
FIG. 5A depicts an exemplary tomosynthesis configuration in which eight imaging sources are arranged in a ring around a multileaf collimator (MLC) that can be used to shape a therapeutic radiation beam.

The number of imaging sources 502 can also be based on the size of the detector (or detectors if more than one is used). FIG. 5B is a simulated image of a detector being illuminated (receiving data) by parallel tomosynthesis. Each square sub-image corresponds to a different x-ray source. Specifically, the eight beams from imaging sources 502 of FIG. 5A may impinge on detector 520 in different sectors/areas of the detector 520. The larger the detector 520, the more non-overlapping beams may be simultaneously received. The central region of the detector remains empty, and could be used for verification of the MV beam (i.e., therapeutic or treatment beam). Tumor images 522 are detected at different angles, and are seen in different sections of the detector. Some of the projections show a clearer view of the tumor than do others, however, all of them are obscured to some degree by the overlying anatomy. They can be combined by tomosynthesis to achieve better visualization of a tumor, as further discussed below.

It is noted that the x-ray sources can remain energized continuously (and detector readouts acquired at the frame rate of the detector), but this could expose the patient to unnecessary amounts of radiation. The energizations could instead be limited to select frames and synchronized to the readout cycle of the detector, so that the sources are energized and de-energized in conjunction with the beginning or end of the detector readout. To reduce scatter from the treatment beam, which may be deleterious to image quality, it may be necessary to de-energize the treatment beam during these frames. It is also noted that not all the x-ray sources need to be energized simultaneously. Certain multi-spot source architectures may require that only one or a small number of sources be activated simultaneously. In some cases, the dwell time per source is substantially shorter than the readout time of the detector; in these cases, the energizations may be sequential but be simultaneous from the viewpoint of the detector. In other cases, groups of sources may be energized at a time. For example, 16 sources could be divided into two groups of 8 sources. In the first frame, one group of sources may be energized, and in the second frame, a second group of sources may be energized. This can be done to increase the field of view on the detector.

Because power is distributed among many x-ray sources, the thermal loading on any individual source can be reduced. Smaller x-ray sources can therefore be used, similar to those used in dental x-ray imaging. Such sources tend to be more compact (such as 7 cm in length by 3.5 cm in diameter) and less expensive than other sources, such as cone beam CT sources. They use stationary instead of rotating anodes. The ring of imaging sources could be placed next to the multileaf collimator, on the side facing the patient. The voltage and current demands on the tube filaments is also much smaller, so a single high voltage generator capable of powering a CT x-ray tube can be repurposed with a switch to instead power, for example, ten smaller dental x-ray tubes. The EPID can likewise be repurposed for tomosynthesis, imaging simultaneously with treatment. The center region of the EPID would be unusable, as it would receive a large flux from the MV photons (of the treatment source). For a collimated SABR treatment, however, the outer regions would be blank and they could receive kV photons (from imaging sources).

To illustrate the viability of real-time tomosynthesis, images have been simulated using publicly available, online CT datasets, including a 4DCT dataset that included images of the tumor in different phases of respiratory motion. In both datasets, the tumor was about 2 cm in diameter. Forward projection was performed to simulate the data acquisition process. Monoenergetic photons were cast through the patient, assuming the attenuation of water was 0.2 cm$^{-1}$ and that attenuation was linear with CT number. The patient was shifted so that the region of interest was at isocenter. Relevant geometric parameters in simulations are listed in Table 1:

TABLE 1

| | |
|---|---|
| kV source-isocenter distance | 40 cm |
| Isocenter-EPID distance | 40 cm |
| Multileaf collimator diameter | 25 cm |
| Source ring diameter (focal spot location) | 30 cm |
| Number of x-ray sources | 8, 16, or 32 |
| EPID detector dimensions | 41 cm by 41 cm |
| Field of view | 5 cm |
| EPID dimensions | 1024 × 1024 pixels |
| Pixel pitch | 400 um |
| X-ray tube size | 7 cm (length) by 3.5 cm (diameter) |

Figure 5C:
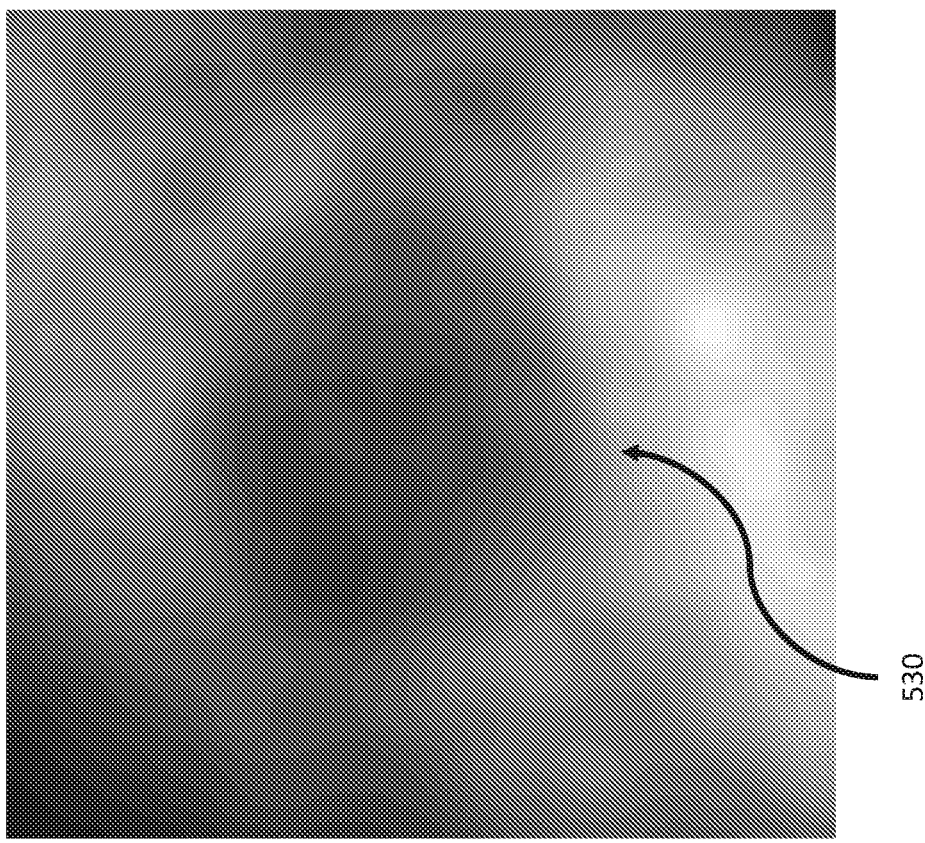
FIG. 5C shows a reconstructed image formed by combining the eight images of FIG. 5B.

Reconstruction from the detector can be done using, for example, shift-and-add, or can be done with filtered back-projection, or with iterative methods. If reconstruction is performed with shift-and-add, a high-pass filter can be used to accentuate detail in the plane of focus. Here, after the detector image was generated, reconstruction was performed by shift-and-add, which is a relatively computationally efficient process. FIG. 5B shows individual images of projection radiography from different angles, and 5C shows an example of these detector images summed together for reconstruction, with improved contrast. In other images presented in this work, shift-and-add is followed by a high-pass filter, which is equivalent to a filtered backprojection-type reconstruction. Iterative reconstruction may also be used, but iterative reconstruction at 30 frames per second may be challenging to implement. FIG. 2B provides a radiograph showing a tumor 210, partially obstructed by overlying anatomy. FIG. 5C provides a zoomed-in image from real-time tomosynthesis (with tumor 530 near the center), produced by shifting and adding the sub-images shown in FIG. 5B prior to any high-pass filter. The tumor is better resolved in FIG. 5C than the tumor in FIG. 2B.

The quality of tomosynthesis depends in part on the number of views used to generate the image. By comparing different configurations, different tradeoffs in image quality and complexity can be observed. One potential configuration is to array the imaging x-ray sources in a simple ring. With the assumptions in Table 1, there is enough room on the EPID for approximately eight images without any overlap. The ring is wide enough so that the ring does not block the exit path from the multileaf collimator. The x-ray sources are small enough so that there is no crowding in the source ring. As a single dental x-ray tube requires half the filament current and a quarter of the filament voltage of a more powerful CT x-ray tube, the eight small tubes can be powered using the same x-ray generator already used for the onboard CBCT (cone beam computed tomography) scanner.

To achieve a greater number of views, a ring configuration with 16 sources may be used in various implementations. To prevent overcrowding of the detector (or overlapping images), each source may be energized only in every other view. Assuming half are energized in each view, the imaging time in this arrangement would be half the frame rate of the EPID. Such a configuration may include a high-voltage switch working in synchrony with the detector, and the switch may add a modest amount of hardware complexity in certain implementations. Further increasing the view count (for example, 24 or 32 sources) is also possible. Significantly more than 24 sources may lead to overcrowding of the source ring, or collision of the tubes. This could be mitigated by arranging the tubes in layers, but this would tend to increase the thickness of the source ring.

Extended image guidance for radiation therapy could impart additional dose to the patient. Even if this dose is much smaller than the therapeutic radiation, unnecessary dose should be avoided when possible. In examining the effect of different power levels on the reconstructed images, it can be observed that the absorbed dose is proportional to the power on each source. It is also observed that x-ray tube cooling requirements may limit the total power available to the system. In simulations, Poisson noise was injected into the detected images according to the number of photons reaching the detector.

It was assumed that the fluence arriving on the detector was $5\times10^5$ photons/mAs-mm$^2$ at a distance 80 cm from the focal spot. The conversion factor varies depending on added filtration and tube design, but this is a reasonable estimate for a tube operating at 80 kVp (kilovoltage peak). It was assumed that the pulse duration in all cases was 25 ms and that the tube power was set to either 0.5 mA or 2 mA. Hence, for the assumed pixel pitch of 400 μm, the number of photons reaching the detector in the absence of patient attenuation is either 1000 or 4000 per frame. Images from both the AP and lateral direction were examined. In the lateral direction, patient attenuation is much higher and hence higher doses could be necessary to ensure adequate visualization.

Figure 6:
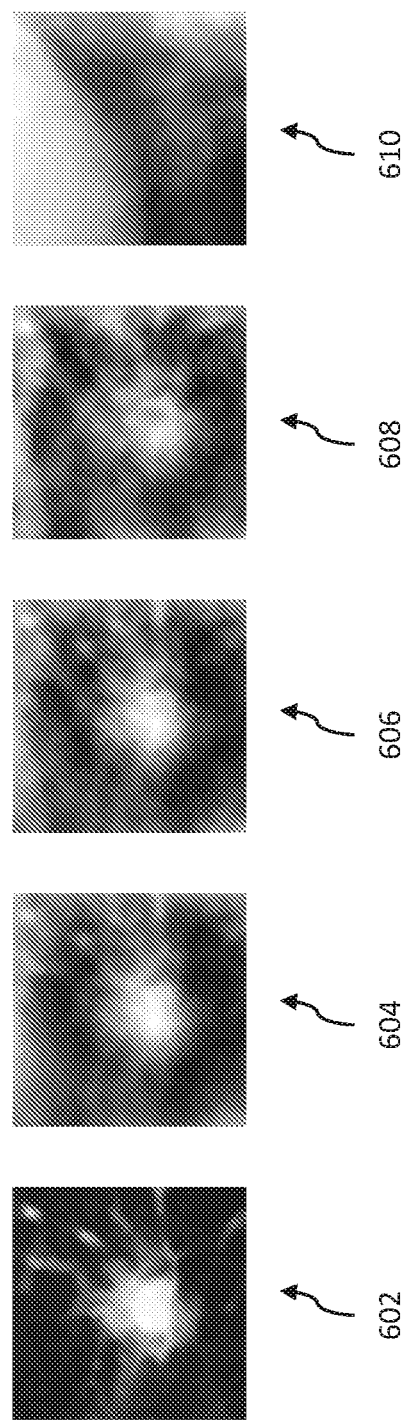
FIG. 6 illustrates contrast of a tumor as a function of the number of x-ray tubes (imaging sources) used. The field of view is 5 cm.

FIG. 6 shows a comparison between real-time tomosynthesis and the source CT dataset as well as fluoroscopy. Specifically, the contrast of a tumor as a function of the number of x-ray tubes used is shown. From left to right, FIG. 6 shows: 1 cm CT slice (602); 32 views (604); 16 views (606); 8 views (608); and 1 view (i.e., fluoroscopy) (610). While the tumor is virtually invisible on fluoroscopy (610), its location can be seen with tomosynthesis (604, 606, 608). The image quality is better with a greater number of views, but the frame rate is reduced for images shown. Assuming a detector frame rate of 30 fps, using 8, 16, or 32 views would yield a system frame rate of 30, 15, or 7.5 fps, respectively. A reduction of frame rate may be unacceptable in case of excessive motion. It is noted that the high-pass filter used to isolate the plane of interest has yielded some artifacts in the images, such as a dark region around the lesion.

Figure 7:
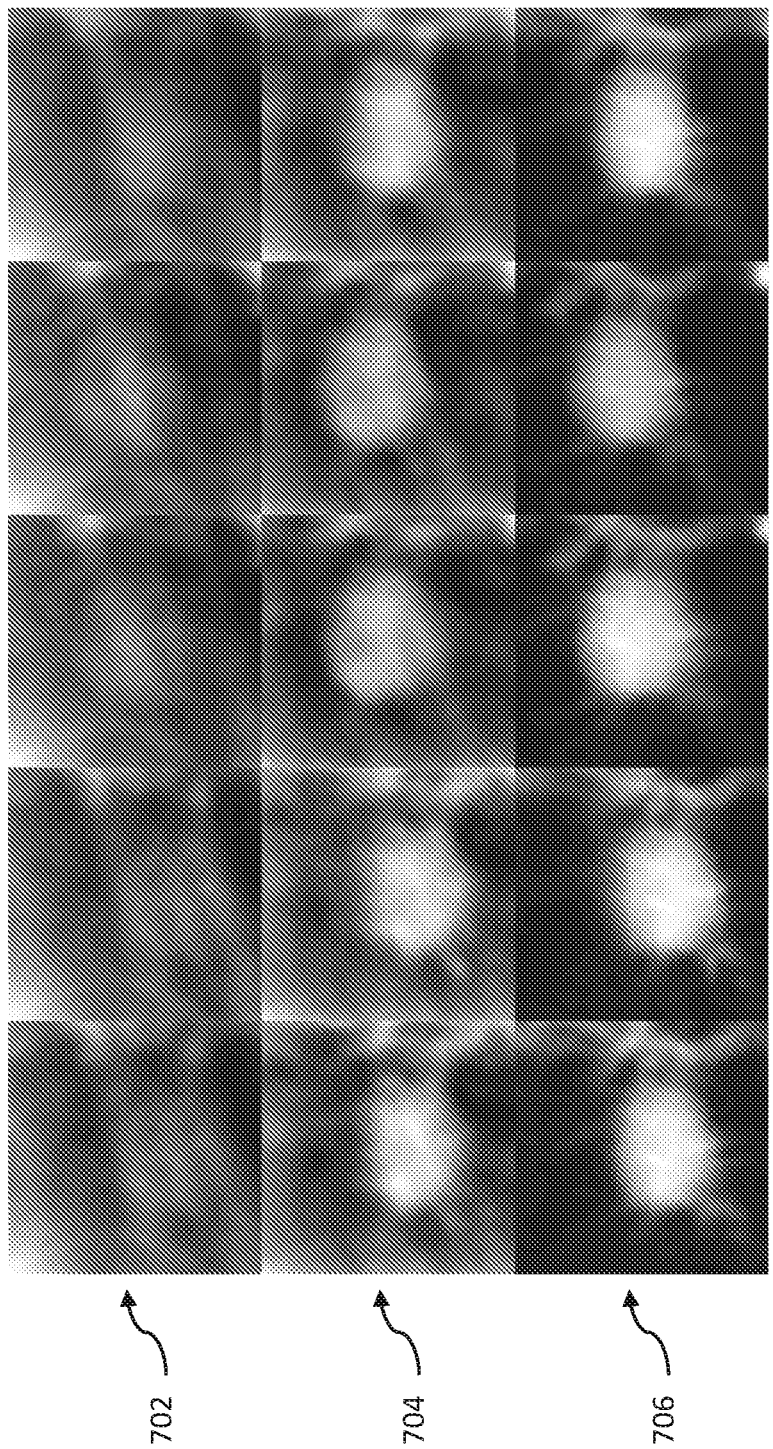
FIG. 7 illustrates real-time tomosynthesis used to track a moving lung tumor. Columns denote different time points of the tumor motion. The top row corresponds with fluoroscopy, the middle row corresponds with real-time tomosynthesis, and the bottom row corresponds with source 4DCT datasets, 1 cm thick slices. The field of view is 5 cm.

FIG. 7 shows an example of tracking the same lung tumor over time. Different phases of a 4DCT series were used to generate the simulations. Columns denote different time points of the tumor motion. The top row (702) corresponds with fluoroscopy, the middle row (704) corresponds with real-time tomosynthesis involving 16 x-ray sources, and the bottom row (706) corresponds with source 4DCT datasets. The tumor can be seen with fluoroscopy (702), but its visibility is limited compared to real-time tomosynthesis (704).

Figure 8:
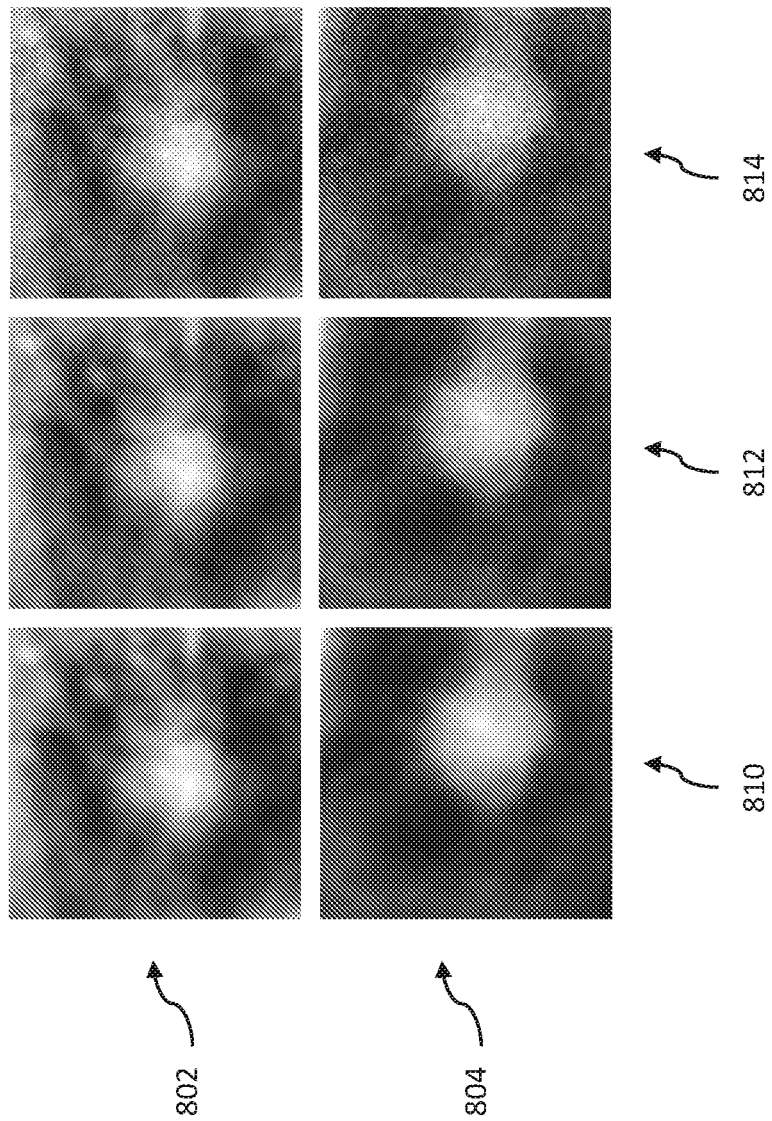
FIG. 8 illustrates the impact of tube power on real-time tomosynthesis. The top row shows AP (anteroposterior) projection, while the bottom row shows the lateral projection.

FIG. 8 shows images of real-time tomosynthesis corresponding with the use of 16 views (15 fps), from both the lateral and AP (anteroposterior) directions, shown with two different power levels as well as the noiseless case. The top row (802) shows AP projection, while the bottom row (804) shows the lateral projection. The left column (810) is the noiseless case (i.e., without any added noise). The middle column (812) includes noise corresponding to each tube operating at 2 mA, or 60 W average power draw. The right column (814) includes noise corresponding to each tube operating at four times less power. In the higher power setting, each of the 16 sources was energized for 25 ms at 2 mA and 80 kVp. In the lower power setting, each source was set to 0.5 mA. At any point in time, the total power draw of the source ring will be 8 times higher because 8 sources are active. However, because each source is tightly collimated, the dose imparted to the patient will be relatively small.

At the lower power setting, because the duty cycle on each tube is about 40%, the average power draw for any individual tube is 15 W. The tumor is highly visible even at 15 W of power per tube. It is noted that in video mode, the observer may be able to tolerate higher levels of image noise than are present in still images.

Figure 9:
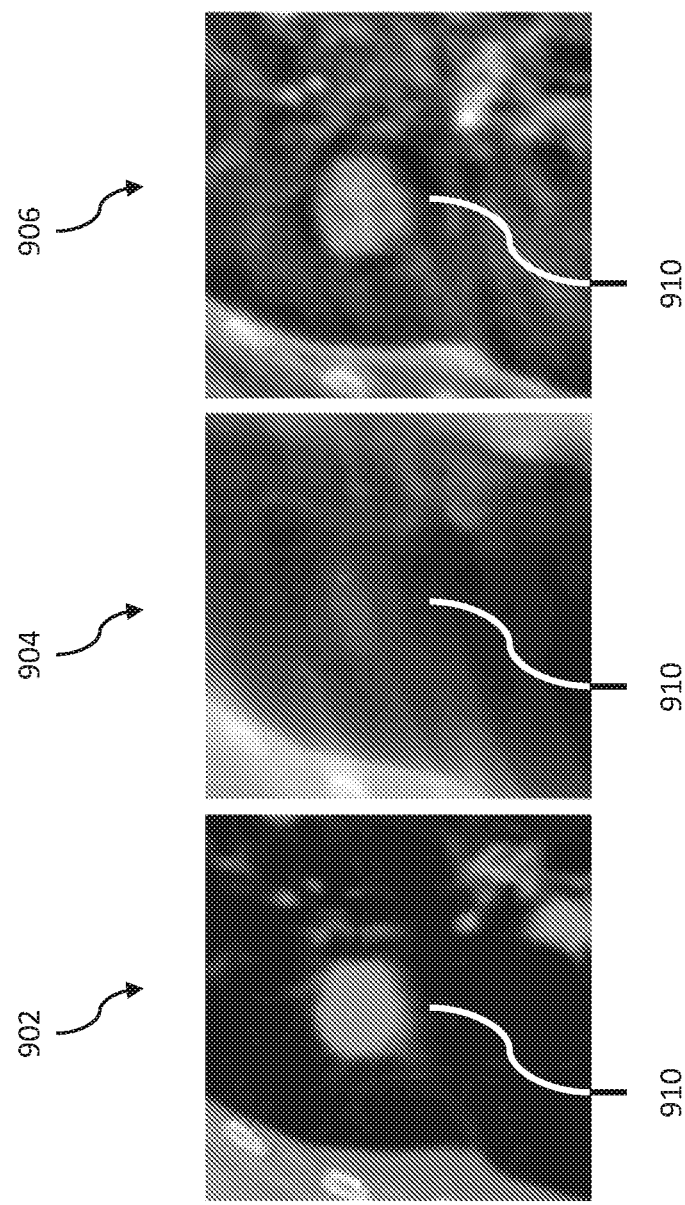
FIG. 9 provides, for comparison, a baseline CT image of a possible lung tumor, a simulated projection radiograph of the same lung tumor, and a simulated parallel tomosynthesis image.

For comparison, FIG. 9 provides a baseline CT image (902) of a possible lung tumor 910, a simulated projection radiograph (904) of the same lung tumor 910, and a simulated parallel tomosynthesis image (906) showing the tumor 910. 16 sources are used, and a high-pass filter is also included in the reconstruction to accentuate detail in the plane of focus. The overlying bone ribcage is largely eliminated.

Figure 10:
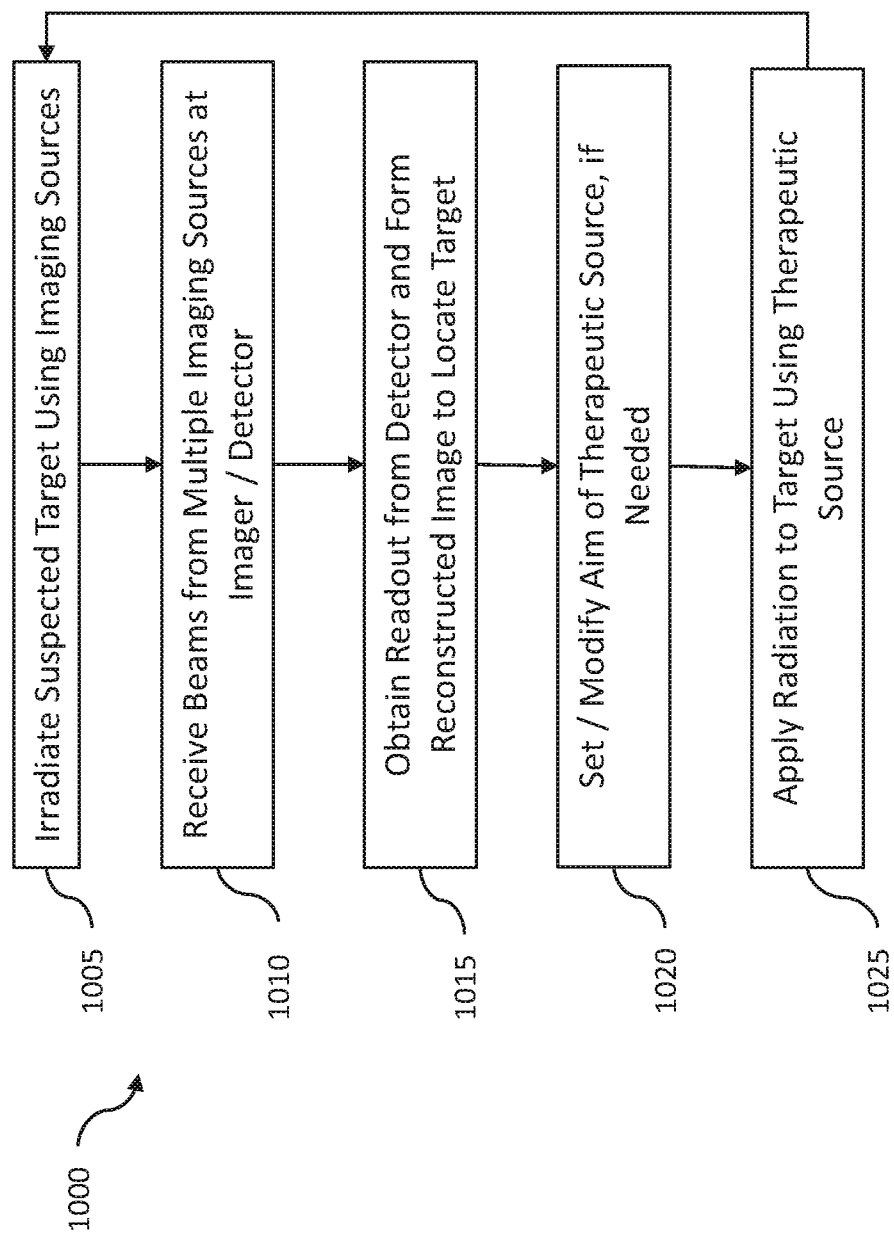
FIG. 10 provides a process of using an exemplary tomosynthesis system to aid in targeting of a treatment beam in radiation therapy.

An exemplary tomosynthesis process 1000 is depicted in FIG. 10. To locate a target, a region of interest suspected of having the target can be simultaneously illuminated with multiple imaging sources (1005), such as kV x-rays that are situated about a treatment source, such as a MV x-ray (capable of emitting high-energy treatment radiation that is, for example, above 200 keV). The beams from the multiple imaging sources can be received at one or more imagers/detectors (1010), such as a detector that is sectored so that area that is not otherwise used by a treatment source is sectionalized for the imaging sources. A readout from the detector containing the multiple images/projections from the imaging sources can be acquired, and images combined to form a reconstructed image (1015) using, for example, a shift-and-add procedure. It is noted that if the detector functions at 30 fps, the detector could be set to acquire 30 readouts per second. The reconstructed image could be analyzed to locate the tumor; this could be performed automatically using, for example, computer vision/image recognition, or via recognition by a user (such as a radiologist) and identification of the tumor (or a portion of the image showing the tumor) via a user input device (such as a mouse, touch screen, etc.).

The direction/aim of the treatment source, such as a MV x-ray, can be set or adjusted as needed (1020) so as to align the treatment beam to maximize overlap with the target (e.g., a tumor) and minimize overlap with surroundings (such as normal or otherwise not-targeted tissue). The treatment/therapeutic source can then be used to apply radiation to the target (1025). Either simultaneously with the application of radiation, or thereafter, the region of interest may be irradiated again using the imaging sources (1005), and the process iteratively repeated (with location of tumor and adjustment of treatment source) for the duration of a treatment regimen. The operation of the imaging sources can be controlled by a controller (such as x-ray controller 130 in FIG. 1A) that controls the treatment source, or in other implementations, using a separate controller in communication therewith. A controller may include, for example, a processor and memory with instructions executable by the processor to perform the above functions. The controller may be implemented using hardware, software, or a combination thereof.

It is noted that the location and size of the field of view can be set so that it encompasses the potential locations of the moving target. For example, if during normal breathing, the tumor may rise and fall across a distance of 3 cm, then the field of view may span a height of 3 cm. Although the imaging sources are at lower energies than the treatment sources, unnecessary exposure to x-rays should be avoided. Consequently, the field of view can be configured, in certain implementations, to be adjustable as warranted. For example, if a patient's breathing changes such that the tumor no longer rises and falls across a span of 3 cm but rather 2 cm (e.g., if the patient relaxes and starts taking shallower breaths), then the field of view can be shrunk (for subsequent images) to reduce the volume receiving imaging x-ray beams. Similarly, because it is possible for a patient to move so that the tumor reaches an "outlier" position (e.g., if the patient has a muscle spasm or is bumped), the system may be configured to resist expanding the field of view unless a target moves beyond the existing field of view a predetermined number of times or for a predetermined length of time. In other words, in exemplary configurations, the system need not "look" where the target is not expected to be (or is unlikely to be in the future), because "looking" in such places unnecessarily exposes the patient to more radiation.

Applied to radiation therapy, components that already exist on the linac may be repurposed, including the high-voltage power generator and the EPID. The additional hardware used, if not already included, is an imaging source ring (including, for example, 8 to 16 dental x-ray tubes in a single housing) and a collimator. The source ring and collimator could be placed directly on top of the existing multileaf collimator, and could be engineered to add, for example, 4 cm of thickness to the multileaf collimator. Moreover, a high speed kV/MV detector (or EPID)—i.e., a detector that can detect both kV photons and MV photons—may be used.

While imaging from the beam's eye view is desirable, in some cases it may be more convenient to image from other directions. In some cases, an auxiliary detector and source are part of the treatment system. This could include the cone-beam CT imager, or it could be a secondary system permanently affixed to the room. In these cases, a source ring and collimator could be installed in proximity to the original source. Depending on the need, the system could either select the original source for a full, field of view image, or it could select the source ring to produce tomosynthesis in a reduced field of view.

The above approach can be applied to many different treatment applications. In cases of motion management by limitation (in particular, patient-initiated breath hold), exemplary tomosynthesis systems could serve as a verification device that could promptly halt treatment if the tumor is out of the ITV. In motion-inclusive or respiratory-gated treatments, the ability to follow the tumor motion track in real-time could potentially allow for a decrease in the ITV and planning target volume (PTV) margins. Clinically, this would reduce the volume of normal lung treated, thus possibly reducing the risk of radiation pneumonitis. In the case of central tumors, this approach may allow tumors previously deemed "too close" to central airways or major vessels to be more safely treated. As compared with external surrogates, direct visualization may enable greater accuracy of tumor tracking. Real-time tomosynthesis is also likely more comfortable for patients than some existing options for motion management, such as abdominal compression or active breathing control.

Simulated images of real-time tomosynthesis show good image quality and contrast of the lung tumors, with a noticeable improvement over fluoroscopy. The lung is a particularly useful case because lung nodules have strong contrast against the background. Whereas fluoroscopy might not be able to identify certain central lung tumors due to poor contrast, the real-time tomosynthesis approach discussed can be utilized in such cases. Because the contrast in the lung is so high, and because several tubes are used simultaneously, the power demanded from each tube is relatively low, enabling the use of compact, stationary anode x-ray tubes.

Compared to conventional tomosynthesis, the exemplary systems for real-time tomosynthesis disclosed involves acquisition of images much more quickly, but the field of view may be relatively smaller with one sectored detector. This makes it well-suited for lung SABR treatments, where the tumors treated tend to be relatively small (i.e., under 5 cm). Because the field of view is smaller, the dose imparted by real-time tomosynthesis may be relatively small compared to fluoroscopy. For example, while eight tubes may be activated simultaneously, for any given power level, the dose-area-product of a single tube will be 16 times less because only a small portion of the detector will be irradiated. In addition, the example studied showed good visualization of the tumor even at less than 1 mA. The EPID sometimes includes a thin sheet of copper to improve detection efficiency of MV photons. This copper was not modeled in simulations discussed here but could impede the detection of kV photons. This effect could be reduced or eliminated if the copper sheet were retracted. For 60 keV photons, 1 mm of copper would absorb approximately 75% of the incident photons. If the copper were not retracted, the dose and power requirements of real-time tomosynthesis would likely be higher but may still be acceptable.

In alternative implementations, the real-time tomosynthesis approach is not limited to radiation therapy. The approach is applicable to, for example, interventional radiology. In this context, a moving field of view may be desired to track an instrument. This can be achieved by attaching the collimator to a three-axis motor and using it to follow the volume being imaged. A mechanized collimator could also be used for the treatment of tumors that are not at isocenter. In some applications, the use of multiple detectors or reduced magnification may be necessary to enlarge the field of view. In other implementations, the above approach may be applied to ablation for arrhythmia, something that requires careful image guidance due to rapid cardiac motion. Also, the spine is a common target for SABR and demands high accuracy, and as a high-contrast object, it could be tracked using tomosynthesis. Outside of radiation therapy, minimally invasive interventions may be guided using real-time tomosynthesis. For example, exemplary tomosynthesis devices could be used to obtain diagnostic images in the thorax with a minimum amount of motion.

Exemplary systems and methods for tomosynthesis are capable of imaging a small field of view at the full frame rate of the detector. In various implementations, the approach uses parallel acquisition of multiple frames by simultaneously illuminating the field of view with multiple sources. EPIDs, or kV/MV detectors, used in linear accelerators can operate at up to 30 fps. For a modest number of views, the imaging time with tomosynthesis will therefore be on the order of a second, which may be insufficient to resolve respiratory motion. In light of this constraint, exemplary implementations may use a single detector readout to measure multiple views simultaneously. In the lung, for example, SABR is usually applied only for tumors with diameters measuring 5 cm or less. The EPID may measure, for example, 41 cm by 41 cm in area. The EPID thus has the surface area to resolve multiple non-overlapping projections of the small tumor.

In other implementations, a device for parallel tomosynthesis includes a plurality of x-ray sources that are energized simultaneously or in rapid succession, causing an object being scanned to be illuminated from multiple viewpoints. The resulting detector will include the x-ray projections (or shadow images) from all the sources, where the projections are located at different parts of the detector image (because the detector is sectored). One detector readout is thus sufficient to acquire multiple views that can be used to reconstruct an entire tomosynthesis image. This reduces the number of detector readouts necessary, and enables tomosynthesis at frame rates sufficient to capture, for example, respiratory or cardiac motion. It is possible to build a plurality of x-ray sources that are simultaneously energized. However, it is also possible to toggle between the miscellaneous x-ray sources in rapid succession, such that a plurality of these sources is energized within the time frame of a single detector readout. In both cases, the advantage of real-time, parallel tomosynthesis may be realized.

Exemplary x-ray sources surround a radiation therapy delivery device that transmits high-energy radiation, often photons in the megavoltage range, using a mechanism such as a linear accelerator or a radioisotope. Examples of these devices include external beam radiation therapy machines or robotic radiosurgery systems. The x-ray radiation from each source is collimated so that the images from each view end on different portions of the detector. Reconstruction would be simpler if the images for each view are separate and distinct from each other, although some overlap of the projection images may be tolerated. Because the x-ray sources are illuminated simultaneously, simpler and lower power x-ray sources can be used. For example, standard stationary anode x-ray tubes may also function well.

In the context of radiation therapy delivery, it may be advantageous to use the detector ("EPID" in external beam radiotherapy) already present on some systems to detect the high-energy beam because this type of detector is able to image megavoltage photons as well as kilovoltage photons. Especially in stereotactic radiotherapy or radiosurgery applications, the high-energy treatment beam may be contained so that only a small field of view is exposed to therapeutic radiation, while most of the field of view of the detector is unused. The regions near the periphery of the detector could be repurposed and detect kilovoltage diagnostic x-ray photons for exemplary implementations of the tomosynthesis approach disclosed here. This can be done simultaneously with radiation treatment, or time for the tomosynthesis and the time for radiation treatment could be interlaced.

In external beam radiation therapy devices in particular, the introduction of real-time tomosynthesis could have relatively modest hardware requirements. Many of these machines already have EPIDs, x-ray generators, and flat panel detectors. A ring of stationary anode x-ray sources could be wired together on the treatment arm. These sources may be on the order of an inch in diameter and would be fairly compact. These sources would be positioned around the multileaf collimator, and they themselves would be collimated down to a small region in isocenter. During treatment, these sources would be periodically pulsed and the EPID detector would be read out. The central portion of the EPID could be used for treatment verification, but the outer portions would contain data for several views and can used for tomosynthesis.

In radiosurgery devices that do not rigidly fix the patient down, positioning accuracy is also critical. A new detector arm could be built and could house a series of smaller kV detectors, or a single large kV/MV detector that would also perform verification of the treatment beam.

Tomosynthesis performed in this manner would capture the tumor from the perspective of the treatment beam and would thereby be directly relevant for treatment. Motion of the tumor can be used to inform the location of radiation treatment. For example, for systems using multileaf collimators, the leaf positions could be adjusted to follow the tumor. Alternatively, the treatment itself could simply be gated. It is noted that if the target moves parallel with the treatment beam (i.e., forwards or backwards), the treatment source need not be re-aimed because the target would remain in the path of the treatment beam. If, however, the target moves left/right or up/down, then the treatment beam may be shifted accordingly to better track the target.

This type of tomosynthesis may have other applications in diagnostic radiology. It can be used to take a single frame in the presence of respiratory or cardiac motion with much higher temporal resolution than architectures which require multiple detector readouts and possibly motion of the x-ray source.

In other configurations, several small detectors can be operated in parallel. These detectors could be spaced farther apart, increasing the tomographic angle and hence the image quality in some applications.

In certain implementations, performing parallel tomosynthesis as described above may limit the number of views that can be simultaneously acquired. To improve the image quality, it may be desirable to group the x-ray sources into a number of subsets, and to fire each subset at a time. For example, if N sources were labeled 1, 2, 3 . . . N, then one imaging strategy is to energize the odd sources in the first detector readout, and the even sources in the next detector readout. This would increase the number of views but would require two readouts.

The present disclosure has described one or more preferred embodiments, and it should be appreciated that many equivalents, alternatives, variations, and modifications, aside from those expressly stated, are possible and within the scope of the invention.

The invention claimed is:

1. An apparatus for tomosynthesis imaging, comprising:
a plurality of imaging sources configured to, when energized, emit radiation beams intersecting at a field of view and projecting images onto an imager having a detection area;
a collimator configured to collimate the radiation emanating from each imaging source such that the radiation from any single imaging source encompasses an area substantially smaller than the detection area; and
a controller configured to:
energize the plurality of imaging sources simultaneously;
acquire readouts from the imager at a frame rate, each readout including images corresponding to each energized imaging source; and
combine the acquired images to generate a reconstructed image.

2. The apparatus of claim 1, wherein a reconstructed image is formed for each detector readout.

3. The apparatus of claim 1, wherein the imaging sources are aligned such that projections thereof are non-overlapping in the detection area of the imager.

4. The apparatus of claim 1, wherein the controller is further configured to estimate a location of a biological target of interest based on the reconstructed image.

5. The apparatus of claim 4, wherein at least one of the plurality of imaging sources includes a high-energy imaging source, and wherein the controller is further configured to determine an adjustment to delivery of high-energy treatment radiation from the high-energy imaging source based on the estimated location.

6. The apparatus of claim 1, further including an imager coupled to the controller and configured to communicate detected images thereto.

7. The apparatus of claim 1, wherein the reconstructed image is generated using shift-and-add.

8. The apparatus of claim 1, wherein the reconstructed image is generated using filtered backprojection.

9. The apparatus of claim 1, wherein the reconstructed image is generated using iterative reconstruction.

10. The apparatus of claim 1, wherein the acquired images are combined so as to focus on a targeted feature and de-focus surrounding features.

11. The apparatus of claim 1, wherein the simultaneously energized imaging sources are energized simultaneously in rapid succession.

12. The apparatus of claim 1, wherein a first subset of the plurality of imaging sources is energized for a first frame, and a second subset of the plurality of imaging sources is energized for a second frame that is subsequent to the first frame.

13. The apparatus of claim 12, wherein the plurality of imaging sources is partitioned such that each imaging source is included in only one of the first and second subsets.

14. The apparatus of claim 1, wherein each of the imaging sources includes a kilovolt x-ray tube.

15. The apparatus of claim 1, further comprising a treatment radiation source.

16. The apparatus of claim 15, wherein the treatment radiation source is a linear accelerator or high-energy radioisotope source.

17. The apparatus of claim 15, wherein the imaging sources are positioned around the source of treatment radiation.

18. The apparatus of claim 17, wherein the imager is configured to detect both kilovoltage photons and megavoltage photons.

19. The apparatus of claim 1, wherein the imager includes multiple detectors.

20. The apparatus of claim 19, wherein each of the multiple detectors receives projections from a subset of the plurality of the imaging sources.

21. The apparatus of claim 1, wherein the apparatus is configured to be integrated with a radiation therapy system having a high-energy treatment radiation source such that the plurality of imaging sources is arranged around the treatment radiation source.

22. A method of guiding radiation therapy, comprising:
energizing multiple imaging sources simultaneously such that radiation beams emitted by the imaging sources intersect at a field of view and project shadow images onto an imager;
acquiring a readout image from the imager, wherein the readout image includes shadow images corresponding with the multiple imaging sources;
generating a reconstructed image using the shadow images of the multiple imaging sources;
estimating a location of a target of interest;
energizing a treatment source to treat the target of interest with a high-energy treatment radiation; and
adjusting delivery of the high-energy treatment radiation to the target of interest based on the estimated location.

23. The method of claim 22, wherein the multiple imaging sources are arranged about the treatment source, wherein the treatment source is used to deliver the high-energy treatment radiation.

24. The method of claim 22, wherein the target of interest is a tumor.

25. The method of claim 22, wherein the adjusting delivery includes gating the treatment source used to deliver the high-energy treatment radiation.

26. The method of claim 22, wherein the adjusting delivery includes re-aiming the treatment source used to deliver the high-energy treatment radiation.

27. The method of claim 22, wherein the imager is configured to detect both kilovoltage photons and megavoltage photons.

28. The method of claim 22, further comprising displaying the reconstructed image to a user.

29. The apparatus of claim 1, wherein the frame rate is at a speed to compensate for motion of a subject in the readouts from the imager.

30. The apparatus of claim 29, wherein the frame rate provides for the readouts from the imager to be acquired in less than half a second.

* * * * *

UNITED STATES PATENT AND TRADEMARK OFFICE
CERTIFICATE OF CORRECTION

PATENT NO. : 10,850,128 B2
APPLICATION NO. : 16/092689
DATED : December 1, 2020
INVENTOR(S) : Scott S. Hsieh Page 1 of 1

It is certified that error appears in the above-identified patent and that said Letters Patent is hereby corrected as shown below:

In the Specification

Column 7, Line 63, "FIG.SB" should be --FIG. 5B--.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*